United States Patent
Haremza

(10) Patent No.: US 6,867,331 B2
(45) Date of Patent: Mar. 15, 2005

(54) METHOD FOR PRODUCING DEOXYBENZOINS

(75) Inventor: Sylke Haremza, Neckargemünd (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/498,126

(22) PCT Filed: Dec. 6, 2002

(86) PCT No.: PCT/EP02/13883

§ 371 (c)(1),
(2), (4) Date: Jun. 9, 2004

(87) PCT Pub. No.: WO03/053900

PCT Pub. Date: Jul. 3, 2003

(65) Prior Publication Data

US 2005/0004400 A1 Jan. 6, 2005

(30) Foreign Application Priority Data

Dec. 11, 2001 (DE) .......................... 101 60 721

(51) Int. Cl.⁷ ............................................. C07C 45/44
(52) U.S. Cl. ...................... 568/322; 568/335; 568/337
(58) Field of Search ................................ 568/322, 335, 568/337

(56) References Cited

U.S. PATENT DOCUMENTS 3,855,301 A  12/1974  Rizzi ........................... 260/590

FOREIGN PATENT DOCUMENTS

CN    1294114    *  5/2001

OTHER PUBLICATIONS

Hull et al., J. Org. Chem. 10, 288–291 (1945).
Pelter et al., Synthesis, 1793–1802 (1998).

* cited by examiner

Primary Examiner—Johann Richter
Assistant Examiner—Sikarl A. Witherspoon
(74) Attorney, Agent, or Firm—Keil & Weinkauf

(57) ABSTRACT

The invention describes a process for the preparation of 1,2-diarylethanones by reaction of an arylacetonitrile and an aromatic compound and hydrolysis of the ketimine compound formed, where the solvent used for the reaction is at least one dialkyl ether of a mono- or polyalkylene glycol or a cyclic ether having at least two oxygen atoms. The process produces good yields at room temperature, and drying of the solvent is not required.

9 Claims, No Drawings

METHOD FOR PRODUCING DEOXYBENZOINS

The present invention relates to a process for the preparation of 1,2-diarylethanones, which are also referred to as deoxybenzoins. Substituted deoxybenzoins are valuable synthesis intermediates, e.g. for the preparation of isoflavanoids, arylisocoumarins, pyrroles, tolanes, phenylpyranones, arylquinolines, quinazolines and many other compounds.

It is known to prepare deoxybenzoins by acylation of aromatic compounds with arylacetonitriles, cf. e.g. Hull et al., J. Org. Chem. 10, 288–291 (1945); Pelter et al., Synthesis, 1793–1802 (1998). This reaction is known under the name "Hoesch reaction". It is usually carried out in an anhydrous diethyl ether in the presence of an acidic catalyst, in particular hydrogen chloride gas and/or Lewis acids, such as zinc chloride, iron(III) chloride or aluminum trichloride. The known processes have the disadvantage of producing only moderate yields. The reaction times are sometimes long and the reaction procedure is involved.

Surprisingly, we have now found that the reaction of an arylacetonitrile with an aromatic compound in dialkyl ethers of mono- or polyalkylene glycols or cyclic ethers with two or more ring oxygen atoms proceeds rapidly in high yields even at room temperature.

The invention therefore provides a process for the preparation of 1,2-diarylethanones by reaction of an arylacetonitrile and an aromatic compound and hydrolysis of the ketimine compound formed, wherein the solvent used for the reaction is at least one dialkyl ether of a mono- or polyalkylene glycol or a cyclic ether with at least two oxygen atoms.

The aromatic compound has at least one electrophilically substitutable hydrogen atom on an aromatic ring. The aromatic ring is generally benzene, naphthalene or a five- or six-membered aromatic ring which includes one to three heteroatoms chosen from nitrogen, oxygen and sulfur, such as pyrrole, imidazole or the like; preferably benzene.

The aryl radical in the arylacetonitrile is generally phenyl, naphthyl or a five- or six-membered aromatic radical which includes one to three heteroatoms chosen from nitrogen, oxygen and sulfur. The process according to the invention is particularly suitable for the reaction of phenylacetonitriles.

The arylacetonitrile and the aromatic compound can carry, on the aromatic ring or on the aryl radical, one or more substituents which are inert under the reaction conditions and do not impair the reaction according to the invention, such as, in particular, hydroxyl, $C_1$–$C_8$-alkoxy, $C_1$–$C_8$-alkyl, $C_6$–$C_{10}$-aryl, $C_1$–$C_8$-alkylthio, cyano, $C_1$–$C_8$-alkylamino and/or di($C_1$–$C_8$-alkyl)amino. Two substituents on adjacent carbon atoms can be joined together to form a cyclic structure, such as, for example, methylenedioxy.

The process according to the invention is particularly suitable for the acylation of aromatic compounds which have 1 to 3 hydroxyl groups on the aromatic ring, such as 1,2-dihydroxybenzene (resorcinol) or 1,3,5-trihydroxybenzene (phloroglucinol).

Compounds which have been used successfully are phenylacetonitriles which have at least one substituent chosen from hydroxyl and $C_1$–$C_0$-alkoxy, such as 4-hydroxyphenylacetonitrile or 4-methoxyphenylacetonitrile.

Preferred embodiments of the process according to the invention can be illustrated by the following equation:

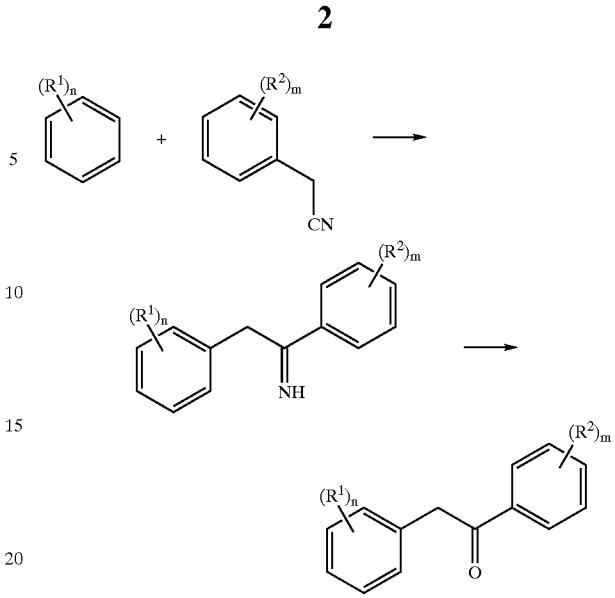

in which $R^1$ and $R^2$, independently, are the abovementioned substituents and n and m are integers from 0 to 3.

The solvent used according to the invention is generally a di($C_1$–$C_8$-alkyl) ether, preferably di($C_1$–$C_4$-alkyl) ether, in particular dimethyl ether or diethyl ether of a poly($C_2$–$C_8$-alkylene) glycol having up to 10 alkyleneoxy units, preferably 2 to 4 alkyleneoxy units. Mono- or polyethylene glycol ethers are preferred. Compounds which have proven particularly useful are diethylene glycol di($C_1$–$C_4$-alkyl) ethers, triethylene glycol di($C_1$–$C_4$-alkyl) ethers and/or tetraethylene glycol di($C_1$–$C_4$-alkyl) ethers. Alternatively, or additionally, it is possible to use cyclic ethers having at least two oxygen atoms in the ring, such as dioxane or crown ethers, e.g. 18-crown-6.

A particular advantage of the process according to the invention is that the solvents used according to the invention for the reaction do not have to be dried. Thus, a water content in the solvent of up to 5% by weight is possible without noteworthy losses in yield.

The reaction according to the invention proceeds in many cases sufficiently rapidly even in the absence of a catalyst. If desired, the reaction according to the invention can be carried out in the presence of an acidic catalyst. A particularly preferred acidic catalyst is hydrogen chloride gas. The hydrogen chloride gas can be suitably bubbled into a solution of the arylacetonitrile and the aromatic compound. Alternatively, or additionally, Lewis acids are also suitable, such as e.g. zinc(II) chloride, iron(III) chloride and aluminum trichloride.

The reaction of the arylacetonitrile and the aromatic compound generally takes place at a temperature of from −25 to 150° C., preferably 0 to 90° C., in particular 10 to 50° C.

The ketimine compound which forms, usually an acid addition salt of the ketimine, is in most cases sparingly soluble in the reaction solution and can be separated off from the mother liquor easily, e.g. by filtration. The mother liquor can advantageously be reused as solvent for the reaction.

The ketimine compound is then hydrolyzed, generally by treatment with water or a dilute aqueous solution of a base, such as sodium hydroxide, sodium carbonate or hydrogen carbonate, or an acid, such as hydrochloric acid. The 1,2-diarylethanone usually separates out of the aqueous phase as a crystalline precipitate and can, where appropriate, be further purified by recrystallization or other purification operations known per se. The ketimine compound can of course also be hydrolyzed without prior separation by adding water or a dilute aqueous solution of an acid, for example, to the reaction mixture. The 1,2-diarylethanone is then isolated by customary methods.

The invention is illustrated in more detail by the examples below:

EXAMPLE 1 (not according to the invention)

54 g (0.4 mol) of 4-hydroxyphenylacetonitrile, 90.8 g (0.72 mol) of phloroglucinol and 8 g (0.06 mol) of zinc chloride were suspended in 700 ml of diethyl ether, and dry HCl gas was introduced at 0 to 5° C. over a period of 6 hours. The mixture was stirred overnight at room temperature, and the residue was filtered off with suction and suspended in 600 ml of 0.2 N hydrochloric acid. The mixture was refluxed for 5 hours. The mixture was then cooled to 20° C. and the precipitate was filtered off with suction, and the residue was washed with 500 ml of water and dried at 100° C. under reduced pressure. Yield 60 g (58%).

EXAMPLE 2 (not according to the invention)

12.6 g (0.1 mol) of 4-hydroxyphenylacetonitrile and 24.3 g (0.18 mol) of phloroglucinol were suspended in 150 ml of diethyl ether, and dry HCl gas was introduced at 0 to 5° C. over a period of 6 hours. The mixture was stirred overnight at room temperature, and the residue was filtered off with suction and suspended in 150 ml of 0.2 N hydrochloric acid. The mixture was refluxed for 5 hours. The mixture was then cooled to 20° C. and the precipitate was filtered off with suction, and the residue was washed with 200 ml of water and dried at 100° C. under reduced pressure. Yield: 18.8 g of a mixture of 20% deoxybenzoin, 20% phloroglucinol and 56% 3,5,3',5'-tetrahydroxydiphenyl ether.

EXAMPLE 3

5.4 g (0.04 mol) of 4-hydroxyphenylacetonitrile and 9.1 g (0.072 mol) of phloroglucinol were suspended in 100 ml of diethyl glycol diethyl ether, and dry HCl gas was introduced at 0 to 5° C. over a period of 6 hours. The mixture was stirred overnight at room temperature, and the residue was filtered off with suction and suspended in 100 ml of 0.2 N hydrochloric acid. The mixture was refluxed for 5 hours. The mixture was then cooled to 20° C. and the precipitate was filtered off with suction, and the residue was washed with 100 ml of water and dried at 100° C. under reduced pressure. Yield: 7.5 g (72%).

EXAMPLE 4 (not according to the invention)

152 g (1 mol) of 4-hydroxyphenylacetonitrile and 110 g (1 mol) of resorcinol are suspended in 340 g (2.4 mol) of boron trifluoride etherate and heated at 70 to 75° C. for 4 hours. The mixture was cooled to room temperature, 1.5 l of saturated sodium hydrogen carbonate solution were added dropwise under a slightly reduced pressure (500 mbar), and the mixture was stirred overnight at room temperature. The precipitate was then filtered off with suction, and the residue was washed with 500 ml of water and recrystallized from 400 g of 1:1 ethanol/water. The residue was dried at 100° C. under reduced pressure. Yield: 137° C. (56%).

EXAMPLE 5

54 g (0.4 mol) of 4-hydroxyphenylacetonitrile and 90.8 g (0.72 mol) of phloroglucinol were dissolved in 400 ml of diethyl glycol diethyl ether, and dry HCl gas was introduced at 20 to 30° C. over a period of 6 hours. The mixture was stirred overnight at room temperature, then the residue was filtered off with suction and suspended in 600 ml of 0.2 N hydrochloric acid. The mother liquor was reused in Example 6. The mixture was refluxed for 5 hours. The mixture was then cooled to 20° C. and the precipitate was filtered off with suction, and the residue was washed with 500 ml of water and dried at 100° C. under reduced pressure. Yield: 81.5 g (78%).

EXAMPLE 6

54 g (0.4 mol) of 4-hydroxyphenylacetonitrile and 50.4 g (0.4 mol) of phloroglucinol were added to the mother liquor from Example 5, and the procedure was continued as in Example 5. The mother liquor was reused in Example 7. Yield: 86.5 g (83%).

EXAMPLE 7

54 g (0.4 mol) of 4-hydroxyphenylacetonitrile and 50.4 g (0.4 mol) of phloroglucinol were added to the mother liquor from Example 6, and the procedure was continued as in Example 5. Yield: 84.5 g (81%).

EXAMPLE 8

13.5 g (0.1 mol) of 4-hydroxyphenylacetonitrile and 22.7 g (0.18 mol) of phloroglucinol were suspended in 100 ml of tetraethylene glycol dimethyl ether, and dry HCl gas was introduced at 20 to 30° C. over a period of 6 hours. The mixture was stirred overnight at room temperature, and the residue was filtered off with suction and suspended in 100 ml of 0.2 N hydrochloric acid. The mixture was refluxed for 5 hours. The mixture was then cooled to 20° C. and the precipitate was filtered off with suction, and the residue was washed with 500 ml of water and dried at 100° C. under reduced pressure. Yield: 20.1 g (77%).

EXAMPLE 9

13.5 g (0.1 mol) of 4-hydroxyphenylacetonitrile and 22.7 g (0.18 mol) of phloroglucinol were dissolved in 100 ml of tetraethylene glycol dimethyl ether, and dry HCl gas was introduced at 20 to 30° C. over a period of 6 hours. The mixture was stirred overnight at room temperature, and the residue was filtered off with suction and suspended in 100 ml of 0.2 N hydrochloric acid. The mixture was refluxed for 2 hours. The mixture was then cooled to 20° C. and the precipitate was filtered off with suction, and the residue was washed with 500 ml of water and dried at 100° C. under reduced pressure. Yield: 20 g (76%).

EXAMPLE 10

13.5 g (0.1 mol) of 4-hydroxyphenylacetonitrile and 22.7 g (0.18 mol) of phloroglucinol were dissolved in 100 ml of tetraethylene glycol dimethyl ether, and dry HCl gas was introduced at 20 to 30° C. over a period of 6 hours. The mixture was stirred overnight at room temperature, and the residue was filtered off with suction and suspended in 100 ml of 0.2 N hydrochloric acid. The mixture was refluxed for 2 hours. The mixture was then cooled to 20° C. and the precipitate was filtered off with suction, and the residue was washed with 500 ml of water and dried at 100° C. under reduced pressure. Yield: 20.3 g (78%).

EXAMPLE 11

13.5 g (0.1 mol) of 4-hydroxyphenylacetonitrile and 12.6 g (0.1 mol) of phloroglucinol were dissolved in 100 ml of tetraethylene glycol dimethyl ether, and dry HCl gas was introduced at 20 to 30° C. over a period of 6 hours. The mixture was stirred overnight at room temperature, and the residue was filtered off with suction and suspended in 100 ml of 0.2 N hydrochloric acid. The mixture was refluxed for 2 hours. The mixture was then cooled to 20° C. and the precipitate was filtered off with suction, and the residue was washed with 500 ml of water and dried at 100° C. under reduced pressure. Yield: 16.6 g (64%).

EXAMPLE 12

The ethereal mother liquor from Example 11 was used once again as solvent in an experiment analogous to Example 11. Yield: 21 g (81%)

EXAMPLE 13 (not according to the invention)

Example 3 was repeated, but using tetrahydrofuran in place of diethylene glycol diethyl ether. No formation of the ketimine hydrochloride was established.

EXAMPLE 14 (not according to the invention)

Example 3 was repeated but using tert-butyl methyl ether in place of diethylene glycol diethyl ether. No formation of the ketimine hydrochloride was established.

EXAMPLE 15 (not according to the invention)

13.5 g (0.1 mol) of 4-hydroxyphenylacetonitrile and 22.7 g (0.18 mol) of phloroglucinol were dissolved in 150 ml of diethylene glycol monomethyl ether, and dry HCl gas was introduced at 20–25° C. over a period of 6 h. The mixture was stirred overnight at room temperature. No formation of the ketimine hydrochloride was observed.

EXAMPLE 16 (not according to the invention)

13.5 g (0.1 mol) of 4-hydroxyphenylacetonitrile and 22.7 g (0.18 mol) of phloroglucinol are dissolved in 150 ml of ethylene glycol, and dry HCl gas was introduced at 20–25° C. over a period of 6 h. The mixture was stirred overnight at room temperature. No formation of the ketimine hydrochloride was observed.

EXAMPLE 17

13.5 g (0.1 mol) of 4-hydroxyphenylacetonitrile and 22.7 g (0.18 mol) of phloroglucinol were dissolved in 150 ml of dioxane, and dry HCl gas was introduced at 20–25° C. over a period of 6 h. The mixture was stirred overnight at room temperature, and the residue was filtered off with suction and suspended in 100 ml of 0.2 N hydrochloric acid. The mixture was refluxed for 2 h. The mixture was then cooled to 20° C. and the precipitate was filtered off with suction, and the residue was washed with 500 ml of water and dried at 100° C. under reduced pressure. Yield: 22 g (84%).

EXAMPLE 18

20.7 g (0.1 mol) of 3,4,5-trimethoxyphenylacetonitrile and 24.3 g (0.19 mol) of phloroglucinol were dissolved in 150 ml of diethylene glycol diethyl ether, and dry HCl gas was introduced at 20–25° C. over a period of 6 h. The mixture was stirred overnight at room temperature, and the residue was filtered off with suction and suspended in 200 ml of demineralized water. The mixture was refluxed for 4 h. The mixture was then cooled to 20° C. and the precipitate was filtered off with suction, and the residue was washed with 200 ml of water and dried at 60° C. under reduced pressure. Yield: 24.6 g (74%).

EXAMPLE 19

13.5 g (0.1 mol) of 4-hydroxyphenylacetonitrile and 22.7 g (0.18 mol) of phloroglucinol were dissolved in 150 ml of dioxane, and dry HCl gas was introduced at 20–25° C. over a period of 6 h. The mixture was stirred overnight at room temperature, and the residue was filtered off with suction and suspended in 200 ml of demineralized water. The mixture was refluxed for 2 h. The mixture was then cooled to 20° C. and the precipitate was filtered off with suction, and the residue was washed with 500 ml of water and dried at 80° C. under reduced pressure. Yield: 20.3 g (78%).

EXAMPLE 20

17.7 g (0.1 mol) of 3,4-dimethoxyphenylacetonitrile and 24.3 g (0.19 mol) of phloroglucinol were dissolved in 150 ml of diethylene glycol diethyl ether, and dry HCl gas was introduced at 20–25° C. over a period of 6 h. The mixture was stirred overnight at room temperature, and the residue was filtered off with suction and suspended in 200 ml of demineralized water. The mixture was refluxed for 4 h. The mixture was then cooled to 20° C. and the precipitate was filtered off with suction, and the residue was washed with 200 ml of water and dried at 80° C. under reduced pressure. Yield: 25 g (82%).

EXAMPLE 21

16.1 g (0.1 mol) of 3,4-methylenedioxyphenylacetonitrile and 24.3 g (0.19 mol) of phloroglucinol were dissolved in 150 ml of diethylene glycol diethyl ether and dry HCl gas was introduced at 20–25° C. over a period of 6 h. The mixture was stirred overnight at room temperature, and the residue was filtered off with suction and suspended in 200 ml of demineralized water. The mixture was refluxed for 4 h. The mixture was then cooled to 20° C. and the precipitate was filtered off with suction, and the residue was washed with 200 ml of water and dried at 80° C. under reduced pressure. Yield: 23.4 g (81%).

I claim:

1. A process for the preparation of 1,2-diarylethanones by reaction of an arylacetonitrile and an aromatic compound and hydrolysis of the ketimine compound formed, wherein the solvent used for the reaction is at least one dialkyl ether of a mono- or polyalkylene glycol or a cyclic ether with at least two oxygen atoms.

2. A process as claimed in claim 1, wherein the solvent used is a diethylene glycol di($C_1$–$C_4$-alkyl) ether, triethylene glycol di($C_1$–$C_4$-alkyl) ether, tetraethylene glycol di($C_1$–$C_4$-alkyl) ether and/or dioxane.

3. A process as claimed in claim 1, wherein the reaction is carried out in the presence of an acidic catalyst.

4. A process as claimed in claim 3, wherein the catalyst used is hydrogen chloride gas.

5. A process as claimed in claim 3, wherein the catalyst used is a Lewis acid.

6. A process as claimed in claim 1, wherein the ketimine compound formed is separated off from the mother liquor and the mother liquor is reused as solvent for the reaction.

7. A process as claimed in claim 1, wherein the aromatic compound has one to three hydroxyl groups on the aromatic ring.

8. A process as claimed in claim 7, wherein the aromatic compound is 1,3,5-trihydroxybenzene.

9. A process as claimed in claim 1, wherein the arylacetonitrile is a phenylacetonitrile which has at least one substituent chosen from hydroxyl and $C_1$–$C_8$-alkoxy on the phenyl radical.

* * * * *